United States Patent [19]

Heeres et al.

[11] Patent Number: 5,710,156
[45] Date of Patent: Jan. 20, 1998

[54] ESTER AND CARBAMATE DERIVATIVES OF AZOLONES

[75] Inventors: Jan Heeres, Vosselaar; Joseph Hector Mostmans, Antwerpen; Robert Jozef Maria Hendrickx, Beerse; Louis Jozef Elisabeth Van der Veken, Vosselaar; Raymond Antoine Stokbroekx, Beerse; Marcel Jozef Maria Van de Aa, Turnhout, all of Belgium

[73] Assignee: Janssen Pharmaceutica N.V., Beerse, Belgium

[21] Appl. No.: 716,397

[22] PCT Filed: Mar. 29, 1995

[86] PCT No.: PCT/EP95/01184

§ 371 Date: Sep. 20, 1996

§ 102(e) Date: Sep. 20, 1996

[87] PCT Pub. No.: WO95/27704

PCT Pub. Date: Oct. 19, 1995

[30] Foreign Application Priority Data

Apr. 6, 1994 [EP] European Pat. Off. .......... 94200938

[51] Int. Cl.$^6$ ............... C07D 403/10; C07D 407/14; A61K 31/495

[52] U.S. Cl. ............... 514/255; 514/318; 544/360; 546/193; 546/194

[58] Field of Search ............ 544/360; 514/255, 514/318; 546/193, 194

[56] References Cited

U.S. PATENT DOCUMENTS

| | | | |
|---|---|---|---|
| 4,791,111 | 12/1988 | Heeres et al. | 514/252 |
| 5,202,346 | 4/1993 | Butera et al. | 514/326 |
| 5,250,528 | 10/1993 | Oku et al. | 514/252 |
| 5,254,553 | 10/1993 | Heeres et al. | 514/252 |

OTHER PUBLICATIONS

H. Rautelin et al., In Vitro Activity of Antifungal Azoles against *Helicobacter pylori*, Eur. J. clin. Microbiol. Infect. Dis., vol. 11, 1992, pp. 273–274.

*Primary Examiner*—Mukund J. Shah
*Assistant Examiner*—Tamthom T. Ngo
*Attorney, Agent, or Firm*—Charles J. Metz

[57] ABSTRACT

The invention is concerned with the compounds having the formula

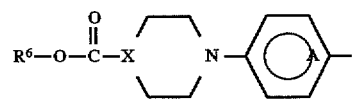 (I)

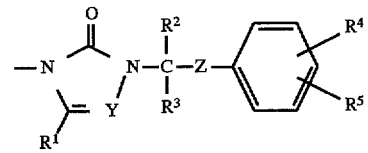

-continued the pharmaceutically acceptable acid addition salts and the stereochemically isomeric form thereof, wherein X and Y are CH or N; $R^1$, $R^2$ and $R^3$ are hydrogen or $C_{1-4}$alkyl; $R^4$ and $R^5$ are hydrogen, halo, $C_{1-4}$alkyl, $C_{1-4}$alkyloxy, hydroxy, trifluoromethyl, trifluoromethyloxy or difluoromethyloxy; $R^6$ is $C_{1-6}$alkyl, hydroxy$C_{1-6}$alkyl, $C_{1-4}$alkyloxy$C_{1-6}$alkyl, phenyl or phenyl$C_{1-4}$alkyl; Z is C=O or CHOH; and

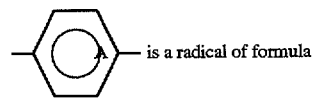 is a radical of formula

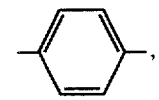 (a-1)

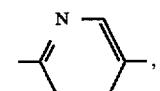

(a-2)

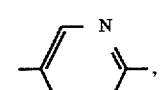

(a-3)

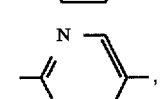

(a-4)

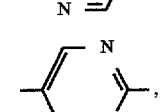

(a-5)

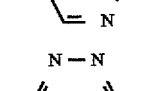

(a-6)

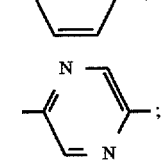

(a-7)

compositions comprising said compounds, processes for preparing the same and the use of these compounds for treating Helicobacter related diseases.

14 Claims, No Drawings

ESTER AND CARBAMATE DERIVATIVES OF AZOLONES

CROSS-REFERENCE TO RELATED APPLICATIONS

This application is based upon PCT Application Ser. No. PCT/EP 95/01184, filed Mar. 29, 1995, which claims priority from European Patent Application Ser. No. 94.200.938.2, filed on Apr. 6, 1994.

The present invention is concerned with substituted azolone derivatives which are potent anti-Helicobacter agents.

U.S. Pat. No. 4,791,111 discloses azolones having a structure similar to that of the present compounds and which are intermediates in the preparation of [[4-[4-(4-phenyl-1-piperazinyl)phenoxymethyl]-1,3-dioxolan-2-yl]methyl]-1H-imidazoles and -1H-1,2,4-triazoles.

In U.S. Pat. No. 4,931,444 there are described substituted azolone derivatives having 5-lipoxy-genase inhibiting activity. The present compounds are distinguished therefrom by their useful anti-Helicobacter activity.

In the eradication of Helicobacter, dual therapies comprising the separate administration of two antibiotic drugs have not been satisfactory because of one or more of the following reasons: a low eradication rate, numerous side effects and development of resistance by Helicobacter. Triple therapies comprising the administration of two antibiotics and a bismuth compound have been shown to be effective, but are very demanding for the patients and are also compromised by side effects. The present compounds show the avantage that they may be used in a monotherapy in the eradication of *Helicobacter pylori* and related species.

The present invention is concerned with compounds having the formula

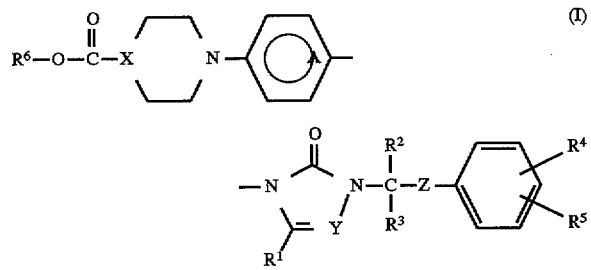

the pharmaceutically acceptable acid addition salts and the stereochemically isomeric forms thereof, wherein X and Y each independently are CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

$R^6$ is $C_{1-6}$alkyl, hydroxy$C_{1-6}$alkyl, $C_{1-4}$alkyloxy$C_{1-6}$alkyl, phenyl or phenyl$C_{1-4}$alkyl;

Z is C=O or CHOH; and

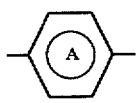

is a radical of formula

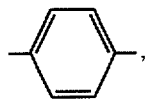 (a-1)

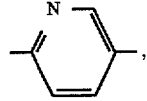 (a-2)

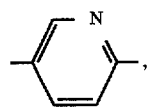 (a-3)

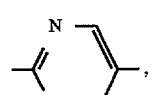 (a-4)

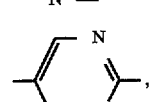 (a-5)

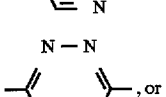 (a-6)

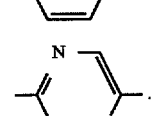 (a-7)

As used in the foregoing definitions halo defines fluoro, chloro, bromo and iodo; $C_{1-4}$alkyl defines straight and branched chain saturated hydrocarbon radicals having from 1 to 4 carbon atoms, i.e. methyl, ethyl, propyl, 1-methylethyl, butyl, 1-methylpropyl, 2-methylpropyl and 1,1-dimethylethyl; $C_{1-6}$alkyl defines $C_{1-4}$alkyl radicals as defined hereinbefore and the higher homologs thereof having from 5 to 6 carbon atoms such as, for example, pentyl and hexyl.

The term pharmaceutically acceptable acid addition salt as used hereinbefore defines the non-toxic, therapeutically active acid addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are inorganic acids such as hydrohalic acid, i.e. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term pharmaceutically acceptable acid addition salts also comprises the solvates which the compounds of formula (I) and the salts thereof may form, e.g. the hydrates, alcoholates and the like.

The term stereochemically isomeric forms as used hereinbefore defines the different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or mixtures thereof are intended to be embraced within the scope of the present invention.

The absolute configuration of each chiral center is indicated by the stereochemical descriptors R and S. For the compounds having two chiral centers, the relative stereodescriptors R* and S* are used in accordance with the Chemical Abstracts rules (Chemical Substance Name Selection Manual (CA), 1982 Edition, Vol. III, Chapter 20).

Some compounds of the present invention may exist in different tautomeric forms and all such tautomeric forms are intended to be included within the scope of the present invention.

A first group of interesting compounds are those compounds of formula (I) wherein $R^6$ is $C_{1-6}$alkyl.

A second group of interesting compounds are those compounds of formula (I) wherein X is N.

A third group of interesting compounds are those compounds of formula (I) wherein

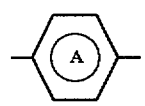

is a radical of formula (a-1) or (a-2).

A fourth group of interesting compounds are those compounds of formula (I) wherein Y is N and $R_1$ is hydrogen.

A fifth group of interesting compounds are those compounds of formula (I) wherein $R^2$ is $C_{1-4}$alkyl and $R^3$ is hydrogen.

A sixth group of interesting compounds are those compounds of formula (I) wherein $R^4$ is halo and $R^5$ is hydrogen or halo.

Preferred compounds are those compounds of formula (I) wherein
$R^1$ and $R^3$ are hydrogen;
$R^2$ and $R^6$ are $C_{1-4}$alkyl;
$R^4$ is halo; and
$R^5$ is halo or hydrogen.

More preferred compounds are those compounds of formula (I) wherein
$R^1$ and $R^3$ are hydrogen;
$R^2$ and $R^6$ are ethyl;
$R^4$ is halo;
$R^5$ is halo or hydrogen;
X and Y are N;
Z is CHOH; and

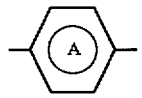

is a radical of formula (a-1) or (a-2).

The most preferred compounds are
ethyl 4-[5-[2-[1-[(4-chlorophenyl)hydroxymethyl]propyl]-2,3-dihydro-3-oxo-4H-1,2,4-triazol-4-yl]-2-pyridinyl]-1-piperazinecarboxylate;
ethyl 4-[4-[2-[1-[(4-chlorophenyl)hydroxymethyl]propyl]-2,3-dihydro-3-oxo-4H-1,2,4-triazol-4-yl]phenyl]-1-piperazinecarboxylate;
ethyl 4-[4-[2-[1-[(4-fluorophenyl)hydroxymethyl]propyl]-2,3-dihydro-3-oxo-4H-1,2,4-triazol-4-yl]phenyl]-1-piperazinecarboxylate;
the pharmaceutically acceptable acid addition salts and the stereochemically isomeric forms thereof.

Analogous procedures for the preparation of compounds such as the present compounds of formula (I) have been described in U.S. Pat. Nos. 4,791,111 and 4,931,444.

In particular, the compounds of formula (I) can be prepared by N-alkylating an intermediate of formula (II) with a reagent of formula (III).

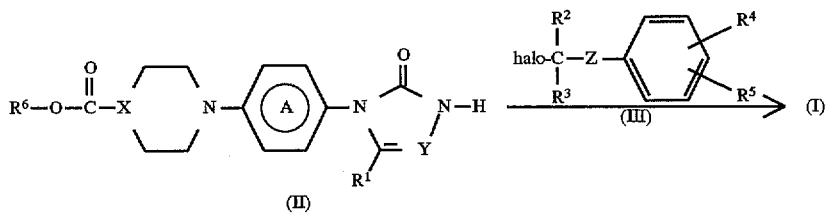

The N-alkylation reaction of (II) with (III) can conveniently be conducted by stirring and heating a mixture of the reagents in an appropriate solvent in the presence of a suitable base. Appropriate solvents are, for example dipolar aprotic solvents, e.g. N,N-dimethylformamide, N,N-dimethylacetamide, 1,3-dimethyl-2-imidazolidinone; aromatic solvents, e.g. benzene, methylbenzene; an ether, e.g 1,1'-oxybisethane, tetrahydrofuran, 1-methoxy-2-propanol; a halogenated hydrocarbon, e.g. dichloromethane, trichloromethane; or a mixture of such solvents.

Suitable bases are, for example, sodium bis(trimethylsilyl)amide, alkali metal and earth alkaline metal carbonates or hydrogen carbonates, e.g. sodium or potassium carbonate; or organic bases, e.g. triethylamine and the like bases.

The compounds of formula (I) wherein X is N, said compounds represented by the formula (I-a), may be prepared by N-acylating an intermediate of formula (IV) with a reagent of formula (V) wherein $L^4$ is a reactive leaving group, such as halo and the like.

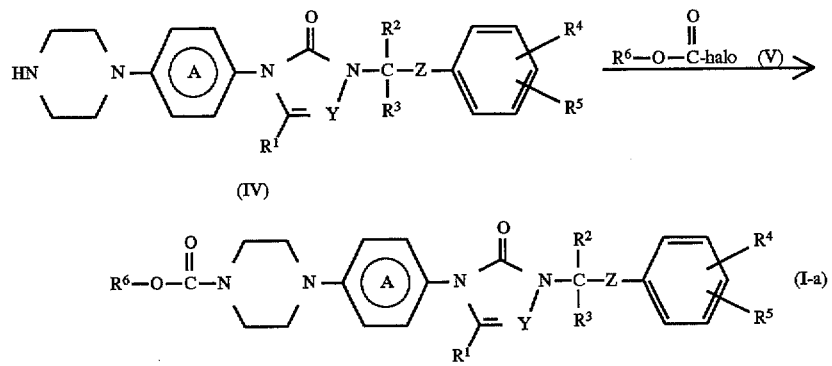

(IV)

(I-a)

The above N-acylation may conveniently be conducted in an appropriate solvent, e.g. dichloromethane, in the presence of a base, e.g. sodium carbonate, triethylamine and the like.

The compounds of formula (I) can also be convened into each other following art-known procedures of functional group transformation.

For example, the compounds of formula (I) wherein Z represents C=O can be converted into the compounds of formula (I) wherein Z represents CHOH following art-known reductions. For example, said reduction can conveniently be conducted by reaction with a metal hydride or complex metal hydride, e.g. sodium borohydride, zinc borohydride, sodium cyanoborohydride and the like in water, N,N-dimethylformamide, 1-methylpyrrolidinone, an alcoholic medium, e.g. methanol, ethanol, or an ether, e.g. tetrahydrofuran, 1,4-dioxane; or in a mixture of such solvents.

Alternatively, said reduction can be conducted by reaction with tris(1-methylethoxy)potassium hydroborate, tris(1-methylpropyl)sodium hydroborate or tris(1-methylpropyl) potassium hydroborate in a reaction-inert solvent, e.g. tetrahydrofuran or N,N-dimethylformamide. Zinc borohydride and tris(1-methylethoxy)potassium hydroborate are suitably used for stereospecific reduction of the carbonyl moiety.

Further, the compounds of formula (I) wherein $R^4$ or $R^5$ is hydroxy can be prepared from the corresponding $C_{1-4}$alkyloxy derivatives by an appropriate dealkylation reaction, for example using trifluoroacetic acid, or in particular a mineral acid such as concentrated hydrohalic acid, e.g. hydrobromic acid, hydroiodic acid, optionally mixed with a saturated solution of hydrobromic acid in glacial acetic acid; a Lewis acid, e.g. boron tribromide in a reaction-inert solvent, e.g. dichloromethane or N,N-dimethylacetamide. In the instance where hydrobromic acid is used it may be advantageous to conduct said dealkylation reaction in the presence of a bromine scavenger such as, for example sodium sulfite or hydrogen sulfite.

The compounds of formula (I) wherein $R^2$ and/or $R^3$ are $C_{1-4}$alkyl can be prepared by the alkylation of the corresponding compound wherein $R^2$ and/or $R^3$ is hydrogen with a suitable alkylating reagent, e.g. a halo$C_{1-4}$alkane, in a reaction-inert solvent, e.g. N,N-dimethylformamide, in the presence of a base, e.g. potassium hydroxide. Optionally, the alkylation reaction may be conducted on a compound of formula (I) wherein $R^6$OOC— is replaced by a suitable protecting group, e.g. a benzyl group. This benzyl derivative may then be converted into the corresponding compound of formula (I) upon reaction with a reagent of formula (V), in a reaction-inert solvent, e.g. dichloromethane, in the presence of a base, e.g. calcium oxide.

Finally, pure isomeric forms of the compounds of formula (I) can be separated from the mixture by conventional separation methods. In particular, the enantiomers may be separated by column chromatography using a chiral stationary phase such as a suitably derivatized cellulose, for example, tri(dimethylcarbamoyl)cellulose (Chiralcel OD®) and similar chiral stationary phases.

In all foregoing and in the following preparations, the reaction products may be isolated from the reaction mixture and, if necesarry, further purified according to methodologies generally known in the art.

Some intermediates and starting materials in the foregoing preparations are known compounds which may be prepared according to art-known methodologies of preparing said or similar compounds. Other intermediates are novel, such as the intermediates of formula (II).

The intermediates of formula (II), wherein X is N, said intermediates represented by the formula (II-a), can be prepared by cyclizing an intermediate of formula (VI) with a reagent of formula (VII) or a derivative thereof.

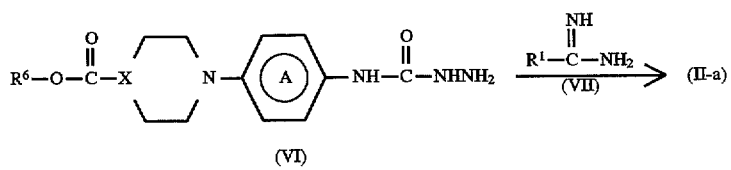

(VI)

An appropriate reaction-inert solvent for the above cyclization reaction is, for example, a dipolar aprotic solvent, e.g. N,N-dimethylformamide, dimethyl sulfoxide and the like, or an alcohol, e.g. ethanol, 1-butanol and the like.

The intermediates of formula (II-a) can be further prepared by cyclizing an intermediate of formula (VIII) with a reagent of formula (IX) wherein $R^7$ is $C_{1-6}$alkyl, e.g. ethyl and $L^1$ is a reactive leaving group, e.g. ethoxy, dimethylamino, and the like, optionally in a reaction-inert solvent, e.g. tetrahydrothiophene 1,1-dioxide.

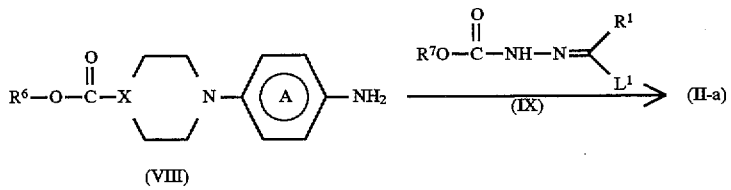

The intermediates of formula (II) wherein Y is CH, said intermediates represented by the formula (II-b), may be prepared by reacting an intermediate of formula (X) with a reagent of formula (XI), wherein $L^2$ and $L^3$ are aldehyde protecting groups, e.g. methoxy, in a reaction-inert solvent, e.g. 1,4-dioxane, yielding an intermediate of formula (XII). The latter intermediate may be cyclized upon treatment with an acid, e.g. formic acid.

pounds of formula (I) were found to show no inhibitory activity against any of the following species: *Campylobactor jejuni, Campylobacter coli, Campylobacter fetus, Campylobacter sputorum, Vibrio spp., Staphylococcus aureus* and *Escherichia coli*, tested at concentrations up to $10^{-5}M$.

An important asset of the present compounds is their sustained activity against *H. pylori* at pH below the neutral

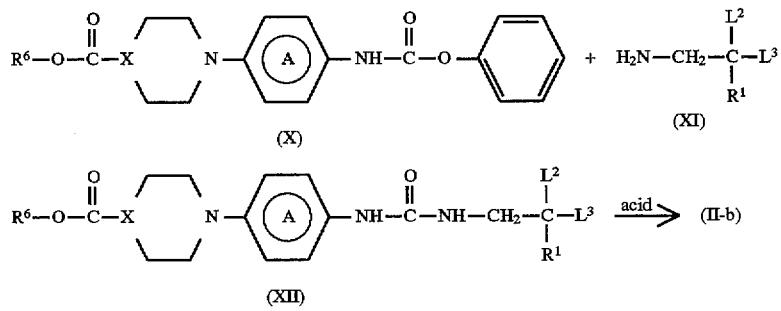

The intermediates of formula (IV) may be prepared by the reaction of a compound of formula (I-a) with an acid, e.g. hydrobromic acid and the like.

pH. Activity at pH below neutral in vitro may indicate that a compound is not adversely affected by the acidic environment of the stomach in vivo.

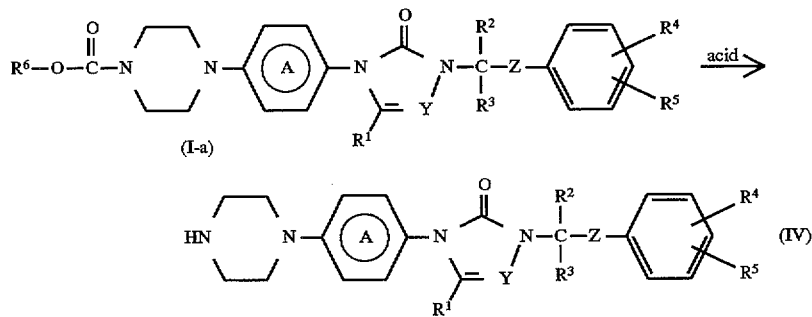

The compounds of formula (I), the pharmaceutically acceptable acid addition salts and the stereochemically isomeric forms thereof display useful pharmacological activity against Helicobacter species, e.g. *Helicobacter pylori, Helicobacter mustelae, Helicobacter felis* and the like, in particular *Helicobacter pylori*.

Particularly important in this context is the finding that the subject compounds show inhibitory activity against the growth of Helicobacter as well as bactericidal activity against said bacteria. The bactericidal effect on Helicobacter was determined with suspension cultures by means of a procedure described in Antimicrob. Agents Chemother., 1991, vol. 35, pp. 869–872.

An interesting feature of the present compounds relates to their highly specific activity against Helicobacter. The com- In view of their useful anti-Helicobacter properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in a dosage form suitable, preferably, for administration orally, rectally, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

When the pharmaceutical composition takes the form of an aqueous solution, those compounds of formula (I) which display low solubility may be formulated as a salt form, or a co-solvent may be added which is water-miscible and physiologically acceptable, e.g. dimethylsulfoxide and the like, or the compounds of formula (I) may be solubilized with a suitable carrier, e.g. a cyclodextrin (CD) or in particular a cyclodextrin derivative such as the cyclodextrin derivates described in U.S. Pat. No. 3,459,731, EP-A-149, 197 (Jul. 24, 1985), EP-A-197,571 (Oct. 15, 1986), U.S. Pat. No. 4,535,152 or WO 90/12035 (Oct. 18, 1990). Appropriate cyclodextrin derivatives are $\alpha$-,$\beta$-,$\gamma$-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are $\beta$-CD, 2,6-dimethyl-$\beta$-CD, 2-hydroxyethyl-$\beta$-CD, 2-hydroxyethyl-$\gamma$-CD, 2-hydroxypropyl-$\gamma$-CD and (2-carboxymethoxy)propyl-$\beta$-CD, and in particular 2-hydroxypropyl-$\beta$-CD.

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin hydroxyalkyl derivatives for use in the compositions according to the present invention the M.S. as determined by mass spectrometry is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. M.S. values determined by NMR or IR preferably range from 0.3 to 1, in particular from 0.55 to 0.75.

The average substitution degree (D.S.) refers to the average number of substituted hydroxyls per anhydroglucose unit. The D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin derivatives for use in the compositions according to the present invention the D.S. as determined by MS is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4. D.S. values determined by NMR or IR preferably range from 0.3 to 1, in particular from 0.55 to 0.75. More particular $\beta$- and $\gamma$-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted $\beta$- or $\gamma$-cyclodextrin is less than 5% of the total cyclodextrin content and in particular is less than 1.5%. Another particularly interesting cyclodextrin derivative is randomly methylated $\beta$-cyclodextrin.

Most preferred cyclodextrin derivatives for use in the present invention are those partially substituted $\beta$-cyclodextrin ethers or mixed ethers having hydroxypropyl, hydroxyethyl and in particular 2-hydroxypropyl and/or 2-(1-hydroxypropyl) substituents.

The most preferred cyclodextrin derivative for use in the compositions of the present invention is hydroxypropyl-$\beta$-cyclodextrin having a M.S. in the range of from 0.35 to 0.50 and containing less than 1.5% unsubstituted $\beta$-cyclodextrin. M.S. values determined by NMR or IR preferably range from 0.55 to 0.75.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

In view of the usefulness of the subject compounds in the treatment of Helicobacter related diseases it is evident that the present invention provides a method of treating warm-blooded animals, in particular humans, suffering from Helicobacter related diseases or afflictions, said method comprising the systemic administration of a pharmaceutically effective amount of a compound of formula (I), a pharmaceutically acceptable acid addition salt thereof or a stereochemically isomeric form thereof, mixed with a pharmaceutical carrier. Examples of said diseases or afflictions are gastritis, stomach ulcers, duodenal ulcers and gastric cancer. In a further aspect of the invention, the subjects compounds are administered for use as a medicine.

In general it is contemplated that an effective daily amount would be from 0.05 mg/kg to 50 mg/kg body weight, preferably from 0.1 mg/kg to 30 mg/kg body weight and more preferably form 0.5 mg/kg to 10 mg/kg body weight.

It is evident that said effective daily amount may be lowered or increased depending on the response of the treated subject and/or depending on the evaluation of the physician prescribing the compounds of the instant invention. The effective ranges mentioned hereinabove are therefore guidelines only and are not intended to limit the scope or use of the invention to any extent.

Optionally, other active compounds used for the eradication of Helicobacter can be administered in combination with the compounds of the present invention. The administration may occur separately (i.e. simultaneously, concurrently or consecutively) or the different drugs may be combined in one dosage form. Suitable compounds for a combination therapy are bismuth compounds, e.g. bismuth subcitrate, bismuth subsalicylate, and the like, antibiotics, e.g. ampicillin, amoxicillin, clarithromycin and the like, $H_2$-receptor antagonists, e.g. cimetidine, ranitidine and the like, and in particular, proton pump inhibitors, e.g. omeprazole, lansoprazole, pantoprazole and the like. For the compounds cited to be useful for a combination therapy with the compounds of formula (I) an effective daily amount would be from 0.05 mg/kg to 50 mg/kg body weight.

Experimental Part

Compounds of formula (I) and some intermediates have a stereogenic center. In those cases where the racemate was separated into its enantiomers, the stereochemically isomeric form which was first isolated was designated as "A" and the second as "B", without further reference to the actual stereochemical configuration.

EXAMPLE 1 a) A mixture of ethyl 4-[5-[(phenoxycarbonyl)amino]-2-pyridinyl]-1-piperazinecarboxylate (0.3 mol crude residue) and hydrazine hydrate (1.5 mol) in 1,4-dioxane (1100 ml) was stirred for 6 hours at room temperature. The reaction mixture was poured into water (4000 ml) and the resulting precipitate was filtered. The filtrate was extracted three times with $CH_2Cl_2$ (700 ml each time). The separated organic layer was washed with water, dried, filtered and the solvent was evaporated. The residue was stirred in DIPE. The precipitate was filtered and dried (25° C.; 20 hours), yielding 62 g (67%) of ethyl 4-[5-[(hydrazinocarbonyl)amino]-2-pyridinyl]-1-piperazinecarboxylate (interm. 9).

In a similar way was prepared:
N-[4-[4-(phenylmethyl)-1-piperazinyl]phenyl] hydrazinecarboxamide (interm. 10).

b1) A mixture of intermediate (9) (0.178 mol) and methanimidamide acetate (0.62 mol) in 1-butanol (800 ml) was stirred and refluxed for 24 hours. The reaction mixture was allowed to cool, then it was poured out into water (500 ml). This mixture was extracted with dichloromethane (2000 ml). The separated organic layer was washed with water, dried ($MgSO_4$), filtered and the solvent was evaporated. The residue was stirred in 2-propanol, filtered and dried (vacuum; 40° C.; 12 hours); yielding 24 g ethyl 4-[5-(2,3-dihydro-3-oxo-4H-1,2,4-triazol-4-yl)-2-pyridinyl]-1-piperazinecarboxylate (42%) (interm. 1).

In a similar way were prepared:
ethyl 4-[5-(1,5-dihydro-3-methyl-5-oxo-4H-1,2,4-triazol-4-yl)-2-pyridinyl]-1-piperazinecarboxylate; mp. 206.9° C. (interm. 3); and
2,4-dihydro-4-[4-[4-(phenylmethyl)-I -piperazinyl]phenyl]-3H-1,2,4-triazol-3-one (interm. 11).

b2) A mixture of ethyl 4-(5-amino-2-pyridinyl)-1-piperazinecarboxylate (0.18 mol) and ethyl 2-[(dimethylamino)methylene]hydrazinecarboxylate (0.54 mol) in tetrahydrothiophene, 1,1-dioxide (50 ml) was stirred at 150° C. for 3 hours. The mixture was cooled till 100° C., 2-propanol was added until crystallization. The precipitate was filtered and recrystallized from methanol; yielding 30.5 g ethyl 4-[5-(2,3-dihydro-3-oxo-4H-1,2,4-triazol-4-yl)-2-pyridinyl]-1-piperazinecarboxylate (53.3%); mp. 220.8° C. (interm. 1).

In a similar way were prepared:
ethyl 1-[4-(2,3-dihydro-3-oxo-4H-1,2,4-triazol-4-yl)phenyl] -4-piperidinecarboxylate; mp. 225.4° C. (interm. 4);
ethyl 4-[4-(2,3-dihydro-3-oxo-4H-1,2,4-triazol-4-yl)phenyl] -1-piperazinecarboxylate; mp. 195.9° C. (interm. 5); and
ethyl 4-[4-(1,5-dihydro-3-methyl-5-oxo-4H-1,2,4-triazol-4-yl)phenyl]-1-piperazine-carboxylate; mp. 204.7° C. (interm. 6).

c) A mixture of ethyl 4-[4-[(phenoxycarbonyl)amino] phenyl]-1-piperazinecarboxylate (0. 1 mol) and 2,2-dimethoxyethanamine (0.2 mol) in 1,4-dioxane (500 ml) was stirred and refluxed for 3 h. The mixture was evaporated, the residue was taken up in formic acid (300 ml) and the mixture was stirred at 60° C. for 2 h. The mixture was evaporated, the residue was taken up in $CH_2Cl_2$, neutralized with a $NaHCO_3$ solution and the precipitate was filtered, yielding 28.5 g (90%) of product. A sample (2g) was crystallized from EtOAc, yielding 1.3 g of ethyl 4-[4-(2,3-dihydro-2-oxo-1H-imidazol-1-yl)phenyl]-1-piperazinecarboxylate; mp. 196.1° C. (interm. 7).

In a similar way was prepared:
ethyl 4-[5-(2,3-dihydro-2-oxo-1H-imidazol-1-yl)-2-pyridinyl]-1-piperazinecarboxylate; mp. 196.2° C. (interm. 8)

d) A mixture of intermediate (1) (0.087 mol), 2-bromo-1-(4-chlorophenyl)-1-butanone (0.097 mol) and sodium carbonate (0.1 mol) in N,N-dimethylformamide (300 ml) was stirred for 6 hours at 80° C. The mixture was cooled, poured into water, extracted with dichloromethane and washed with water. The organic layer was dried, filtered and evaporated. The residue was purified by column chromatography over silica gel (eluent: $CH_2Cl_2/CH_3OH$ 99/1). The pure fractions were collected and evaporated. The residue was crystallized from methanol; yielding: 33.7 g (±)-ethyl 4-[5-[2-[1-(4-chlorobenzoyl)propyl]-2,3-dihydro-3-oxo-4H-1,2,4-triazol-4-yl]-2-pyridinyl]-1-piperazinecarboxylate (78%). A sample (4g) was crystallized from n-butanol; yielding 3.5 g (±)-ethyl 4-[5-[2-[1-(4-chlorobenzoyl)propyl]-2,3-dihydro-3-oxo-4H-1,2,4-triazol-4-yl]-2-pyridinyl]-1-piperazinecarboxylate; mp. 139.1° C. (comp. 1).

EXAMPLE 2 a) A mixture of compound (1) (0.048 mol) in hydrobromic acid, 48% solution in water (250 ml) was stirred and refluxed overnight. The mixture was evaporated, the residue was dissolved in dichloromethane, neutralized with $NH_4OH/H_2O$ and extracted with dichloromethane. The organic layer was washed with water, dried, filtered, and evaporated. A sample (3.5g) of the residue (total 18g) was purified by column chromatography over silica gel (eluent: $CH_2Cl_2/(CH_3OH/NH_3)$ 99/1). The pure fractions were collected and evaporated. The residue was dissolved in 2-propanol and converted into the hydrochloric acid salt (1:1) in 2-propanol. The precipitate was filtered, washed with 2-propanol and dried at 150° C., yielding 1.7 g (±)-2-[1-(4-chlorobenzoyl)propyl]-2,4-dihydro-4-[6-(1-piperazinyl)-3-pyridinyl]-3H-1,2,4-triazol-3-one monohydrochloride (39.4%); mp. 209.8° C. (interm. 2).

b) A mixture of butyl carbonochloridate (0.015 mol), the free base of intermediate 2 (0.013 mol) and sodium carbonate (0.03 mol) in dichloromethane (100 ml) was stirred at room temperature overnight. Water was added and the layers were separated. The organic layer was dried, filtered and evaporated. The residue was crystallized from ethanol. The precipitate was filtered and dried, yielding 3.3 g (±)-butyl 4-[5-[2-[1-(4-chlorobenzoyl)propyl]-2,3-dihydro-3-oxo-4H-1,2,4-triazol-4-yl]-2-pyridinyl]-1-piperazinecarboxylate (48%). The filtrate was evaporated, yielding 3.6 g (±)-butyl 4-[5-[2-[1-(4-chlorobenzoyl)propyl]-2,3-dihydro-3-oxo-4H-1,2,4-triazol-4-yl]-2-pyridinyl]-1-piperazinecarboxylate (52%). Total yield: 6.9 g of (±)-butyl 4-[5-[2-[1-(4-chlorobenzoyl)propyl]-2,3-dihydro-3-oxo-4H-1,2,4-triazol-4-yl]-2-pyridinyl]-1-piperazinecarboxylate (±100%) (comp. 41).

EXAMPLE 3

Compound 1 (0.01 mol) in N,N-dimethylformamide (100 ml) was cooled till −30° C. A 1M solution of tris(1-methylethoxy)potassium hydroborate in tetrahydrofuran (0.02 mol) was added dropwise at −30° C. and the mixture was brought slowly to room temperature. The mixture was poured into water and filtered. The precipitate was purified by column chromatography over silica gel (eluent: $CH_2Cl_2$/$CH_3OH$ 99/1). The pure fractions were collected and evaporated. The residue was crystallized from 2-propanol, yielding 3.2 g (±)-ethyl (R*,R*)-4-[5-[2-[1-[(4-chlorophenyl)hydroxymethyl]propyl]-2,3-dihydro-3-oxo-4H-1,2,4-triazol-4-yl]-2-pyridinyl]-1-piperazinecarboxylate (63.9%); mp. 196.1° C. (comp. 3).

EXAMPLE 4

A mixture of compound (35) (0.02 mol) in hydrobromic acid, 48% solution in water (50 ml) was stirred and refluxed overnight. The solvent was evaporated. The residue was dissolved in dichloromethane. The organic solution was washed with an aqueous $Na_2CO_3$ solution, dried, filtered and the solvent was evaporated. The residue was dissolved in N,N-dimethylacetamide (50 ml). Carbonochloridic acid ethyl ester (3 g) was added and the reaction mixture was stirred for 2 hours. The mixture was poured out into water and stirred for 30 min. The supernatant was decanted and the oily residue was dissolved in dichloromethane. The organic solution was washed, dried, filtered and the solvent was evaporated. The residue was purified twice by column chromatography over silica gel (eluent $CH_2Cl_2$/$CH_3OH$/hexane/ethyl acetate 48/2/20/30). The pure fractions were collected and the solvent was evaporated (for 2 hours at 20° C.). The residue was cooled in a $CO_2$/2-propanol bath. The solid was dried (vacuum; room temperature); yielding: 2.3 g (±)-ethyl 4-[5-[2-[1-(4-hydroxybenzoyl)propyl]-2,3-dihydro-3-oxo-4H-1,2,4-triazol-4-yl]-2-pyridinyl]-1-piperazinecarboxylate (24%); mp. 94.3° C. (comp. 4).

EXAMPLE 5

(±)-ethyl (R*,R*)-4-[4-[2-[1-[(4-fluorophenyl)hydroxymethyl]propyl]-2,3-dihydro-3-oxo-4H-1,2,4-triazol-4-yl]phenyl]-1-piperazinecarboxylate (comp. 63) (0.001 mol) was separated by chiral resolution on CHIRALCEL OD 20 μm® (eluent: hexane/$C_2H_5OH$ 70/30). The pure fractions were collected and evaporated; yielding 0. 18g ethyl [A-(R*,R*)]-4-[4-[2-[1-[(4-fluorophenyl)hydroxymethyl]propyl]-2,3-dihydro-3-oxo-4H-1,2,4-triazol-4-yl]phenyl]-1-piperazinecarboxylate (37.2%); mp. 161.2° C. (comp. 5); and 0.18g ethyl [B-(R*,R*)]-4-[4-[2-[1-[(4-fluorophenyl)hydroxymethyl]propyl]-2,3-dihydro-3-oxo-4H-1,2,4-triazol-4-yl]phenyl]-1-piperazinecarboxylate (37.2%); mp. 151.2° C. (comp. 6).

EXAMPLE 6 a) A mixture of intermediate (11) (0.01 mol) in N,N-dimethylformamide (50 ml) was stirred under N2. A solution of sodium bis(trimethylsilyl)amide in tetrahydrofuran (2M) (0.01 mol) was added dropwise and the mixture was stirred at room temperature for 10 min. 1-(4-Chlorophenyl)-2-bromopropanone (0.015 mol) dissolved in N,N-dimethylformamide was added dropwise and the mixture was stirred at room temperature for 1 h. The mixture was poured into water and stirred. The precipitate was filtered, dissolved in $CH_2Cl_2$, dried, filtered and evaporated to a small volume. The oily residue was purified by column chromatography over silica gel (eluent: $CH_2Cl_2$/hexane/EtOAc 1/2/1). The pure fractions were collected and evaporated. The residue (2.3g) was crystallized from EtOAc, yielding 1.7 g (34%) of (±)-2-[2-(4-chlorophenyl)-1-methyl-2-oxoethyl]-2,4-dihydro-4-[4-[4-(phenylmethyl)-1-piperazinyl]phenyl]-3H-1,2,4-triazol-3-one; mp. 164.3° C. (interm. 12).

b) A mixture of intermediate (12) (0.022 mol) in N,N-dimethylformamide (60 ml) was stirred under N2 at room temperature till most of intermediate (12) was dissolved. Potassium hydroxide (0.025 mol) was added and the mixture was stirred for 5 min. Iodomethane (0.025 mol) dissolved in N,N-dimethylformamide was added dropwise and the mixture was stirred at room temperature for 1 h. The mixture was poured into ice water (500 ml) while stirring and filtered. The precipitate was washed with water on a filter and dissolved in $CH_2Cl_2$. The organic layer was dried ($MgSO_4$), filtered and evaporated. The residue was purified by column chromatography over silica gel (eluent: EtOAc/hexane/$CH_2Cl_2$/$CH_3OH$ 20/30/49/1). Fraction 1 was collected and evaporated. The residue was crystallized from EtOAc, yielding 3.3 g (29%) of product. The product was crystallized again, yielding 2.58 g (23%) of 2-[2-(4-chlorophenyl)-1, 1-dimethyl-2-oxoethyl]-2,4-dihydro-4-[4-[4-(phenylmethyl)-1-piperazinyl]phenyl]-3H-1,2,4-triazol-3-one; mp. 150.3° C. (interm. 13).

c) A mixture of intermediate (13) (0.0145 mol), ethyl chloroformate (0.02 mol) and calcium oxide (5 g) in dichloromethane (150 ml) was stirred overnight at room temperature. The mixture was filtered and the filtrate was evaporated. The precipitate was filtered and crystallized from EtOAc/hexane. The precipitate was filtered and dried, yielding 4.85 g (67.2%) of ethyl 4-[4-[1-[2-(4-chlorophenyl)-1,1-dimethyl-2-oxoethyl]-1,5-dihydro-5-oxo-4H-1,2,4-triazol-4-yl]phenyl]-1-piperazinecarboxylate; mp. 137.0° C. (comp. 78).

EXAMPLE 7

Compound (78) (0.0057 mol) was dissolved in N,N-dimethylformamide (50 ml) upon stirring. Sodium borohydride (0.017 mol) was added and the mixture was stirred at room temperature for 3 h. The mixture was poured into ice water and stirred for 30 min. The precipitate was filtered and recrystallized from EtOAc and DIPE. The precipitate was filtered and dried, yielding 1.8 g (63.2%) of (±)-ethyl 4-[4-[1-[2-(4-chlorophenyl)-2-hydroxy-1,1-dimethylethyl]-1,5-dihydro-5-oxo-4H-1,2,4-triazol-4-yl]phenyl]-1-piperazinecarboxylate; mp. 108.4° C. (comp. 79).

EXAMPLE 8

A mixture of compound (1) (0.0044 mol) in tetrahydrofuran (150 ml) was stirred under $N_2$ at 0° C. on an ice bath. Zinc borohydride (0.0051 mol) was added dropwise at 0° C. and the mixture was stirred at 0° C. for 1 h. The mixture was allowed to warm to room temperature and stirred at this temperature for 1 h. The mixture was evaporated in vacuo and water and $CH_3COOH$ 10% were added to the residue. $CHCl_3$ was added and the layers were separated. The organic layer was dried ($MgSO_4$), filtered and evaporated. The residue (3g) was purified by column chromatography over silica gel (eluent: hexane/EtOAc 20/80). The suitable fractions were collected and evaporated. The oily residue was triturated in water. The precipitate was filtered, washed with water and dried at ° C. overnight, yielding 1.16g (52.6%) (±)-ethyl (R*,S*)-4-[5-[1-[1-[(4-chlorophenyl)hydroxymethyl]propyl]-1,5-dihydro-5-oxo-4H-1,2,4-triazol-4-yl]-2-pyridinyl]-1-piperazinecarboxylate hemihydrate; mp. 118.4° C. (comp. 82).

Tables 1, 2, and 3 hereinbelow summarize the compounds prepared in accordance with one of the above examples.

TABLE 1

R⁶—O—C(=O)—X[piperidine/piperazine]—N—[pyridine/phenyl with Q]—N—[triazolone]—N—CH(CH₂—CH₃)—C(=O)—[phenyl with R⁴, R⁵]

| Co. no | Ex. no | R⁶ | X | Q | R⁴ | R⁵ | Physical data |
|---|---|---|---|---|---|---|---|
| 1 | 1 | CH₃—CH₂— | N | N | 4-Cl | H | mp. 139.1° C. |
| 4 | 4 | CH₃—CH₂— | N | N | 4-OH | H | mp. 94.3° C. |
| 7 | 1 | CH₃—CH₂— | N | CH | 3-Cl | 5-Cl | mp. 133.6° C./HCl |
| 8 | 1 | CH₃—CH₂— | N | N | 3-Cl | 5-Cl | mp. 127.7° C. |
| 9 | 1 | CH₃—CH₂— | N | CH | 2-Br | 4-Br | mp. 125.1° C. |
| 10 | 1 | CH₃—CH₂— | N | CH | 2-F | 4-F | mp. 176.0° C./HCl |
| 11 | 1 | CH₃—CH₂— | C | CH | 4-Cl | H | HCl |
| 12 | 1 | H₃C—O—CH₂—CH(CH₃)— | C | CH | 4-Cl | H | HCl |
| 13 | 1 | CH₃—CH₂— | N | N | 2-Br | 4-Br | mp. 114.9° C. |
| 14 | 1 | CH₃—CH₂— | N | CH | 3-CF₃ | H | mp. 125.2° C. |
| 15 | 1 | CH₃—CH₂— | N | N | 2-F | 4-F | mp. 115.1° C. |
| 16 | 1 | CH₃—CH₂— | N | CH | 3-Br | H | mp. 160.9° C. |
| 17 | 1 | CH₃—CH₂— | N | N | 3-Br | H | mp. 179.3° C. |
| 18 | 1 | CH₃—CH₂— | N | N | 3-CF₃ | H | mp. 146.5° C. |
| 19 | 1 | CH₃—CH₂— | N | CH | 3-Cl | H | mp. 145.7° C. |
| 20 | 1 | CH₃—CH₂— | N | N | H | H | mp. 136.5° C. |
| 21 | 1 | CH₃—CH₂— | N | N | 3-Cl | H | mp. 167.0° C. |
| 22 | 1 | CH₃—CH₂— | N | CH | H | H | mp. 105.1° C. |
| 23 | 1 | CH₃—CH₂— | N | CH | 2-Cl | H | mp. 94.7° C. |
| 24 | 1 | CH₃—CH₂— | N | N | 2-Cl | H | mp. 109.9° C. |
| 25 | 1 | CH₃—CH₂— | N | CH | 4-F | H | mp. 107.6° C. |
| 26 | 1 | CH₃—CH₂— | N | N | 4-F | H | mp. 110.2° C. |
| 27 | 1 | CH₃—CH₂— | N | CH | 3-Cl | 4-Cl | mp. 112.0° C. |
| 28 | 1 | CH₃—CH₂— | N | N | 3-Cl | 4-Cl | mp. 122.0° C. |
| 29 | 1 | CH₃—CH₂— | N | CH | 4-CH₃ | H | mp. 160.1° C./HCl |
| 30 | 1 | CH₃—CH₂— | N | N | 4-Br | H | mp. 150.1° C. |
| 31 | 1 | CH₃—CH₂— | N | CH | 4-Br | H | mp. 121.9° C. |
| 32 | 1 | CH₃—CH₂— | N | CH | 4-O—CH₃ | H | mp. 154.9° C./HCl |
| 33 | 1 | CH₃—CH₂— | N | N | 4-CH₃ | H | mp. 110.6° C. |
| 34 | 1 | CH₃—CH₂— | N | N | 2-Cl | 4-Cl | mp. 175.1° C. |
| 35 | 1 | CH₃—CH₂— | N | N | 4-O—CH₃ | H | mp. 109.2° C. |
| 36 | 1 | CH₃—CH₂— | N | CH | 2-Cl | 4-Cl | mp. 109.3° C. |
| 37 | 1 | CH₃—CH₂— | N | CH | 4-Cl | H | mp. 110.9° C. |
| 2 | 2 | CH₃—(CH₂)₃— | N | CH | 4-Cl | H | mp. 146.4° C./HCl |
| 39 | 2 | CH₃—(CH₂)₂— | N | CH | 4-Cl | H | HCl |
| 40 | 2 | CH₃— | N | CH | 4-Cl | H | mp. 185.2° C./HCl |
| 41 | 2 | CH₃—(CH₂)₃— | N | N | 4-Cl | H | — |
| 74 | 2 | C₆H₅—CH₂— | N | CH | 4-Cl | H | mp. 160.1° C./HCl |
| 75 | 2 | C₆H₅—CH₂— | N | N | 4-Cl | H | |
| 76 | 2 | C₆H₅— | N | N | 4-Cl | H | |
| 77 | 2 | C₆H₅— | N | CH | 4-Cl | H | HCl |
| 83 | 2 | (CH₃)₂—CH— | N | N | 4-Cl | H | mp. 150.3° C. |
| 84 | 2 | CH₃ | N | N | 4-Cl | H | mp. 107.8° C. |
| 85 | 2 | (CH₃)₃—C— | N | N | 4-Cl | H | mp. 160.1° C. |

TABLE 2

R⁶—O—C(=O)—X[piperazine]—N—[pyridine/phenyl with Q]—N—[triazolone]—N—CH(CH₂—CH₃)—CH(OH)—[phenyl with R⁴, R⁵]

| Co no | Ex no | R⁶ | X | Q | R⁴ | R⁵ | Physical data |
|---|---|---|---|---|---|---|---|
| 3 | 3 | CH₃—CH₂ | N | N | 4-Cl | H | mp. 196.1° C./(R*,R*) |
| 42 | 5 | CH₃—CH₂ | N | N | 4-Cl | H | mp. 199.1° C./[A-(R*,R*)] |
| 43 | 5 | CH₃—CH₂ | N | N | 4-Cl | H | mp. 196.5° C./[B-(R*,R*)] |
| 44 | 3 | CH₃—(CH₂)₃ | N | N | 4-Cl | H | mp. 190.1 C./(R*,R*) |
| 45 | 3 | CH₃—CH₂ | N | CH | 3-Cl | 5-Cl | mp. 196.4 C./(R*,R*) |
| 46 | 3 | CH₃—CH₂ | N | CH | 4-Cl | H | mp. 186.1° C./(R*,R*) |
| 47 | 5 | CH₃—CH₂ | N | CH | 4-Cl | H | m . 205.9° C./[A-(R*,R*)] |
| 48 | 5 | CH₃—CH₂ | N | CH | 4-Cl | H | mp. 206.3° C./[B-(R*,R*)] |
| 49 | 3 | CH₃—CH₂ | N | CH | 2-Br | 4-Br | mp. 132.6° C./(R*,R*).H₂O |

TABLE 2-continued

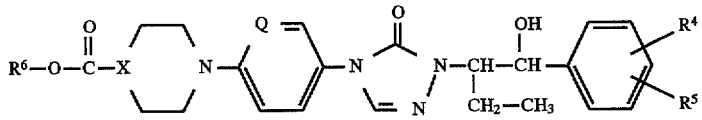

| Co no | Ex no | $R^6$ | X | Q | $R^4$ | $R^5$ | Physical data |
|---|---|---|---|---|---|---|---|
| 50 | 3 | $CH_3-CH_2$ | N | N | 2-F | 4-F | mp. 179.5° C./(R*,R*) |
| 51 | 3 | $CH_3-CH_2$ | N | N | 2-Br | 4-Br | mp. 182.5° C./(R*,R*) |
| 52 | 3 | $CH_3-CH_2$ | N | CH | 3-$CF_3$ | H | mp. 135.1° C./(R*,R*) |
| 53 | 3 | $CH_3-CH_2$ | N | N | 3-$CF_3$ | H | mp. 187.9° C./(R*,R*) |
| 54 | 3 | $CH_3-CH_2$ | N | N | 2-Cl | H | mp. 110.2° C./(R*,R*).½$H_2O$ |
| 55 | 3 | $CH_3-CH_2$ | N | CH | 3-Br | H | mp. 154.8° C./(R*,R*) |
| 56 | 3 | $CH_3-CH_2$ | N | N | 3-Br | H | mp. 173.6° C./(R*,R*) |
| 57 | 3 | $CH_3-CH_2$ | N | CH | 2-Cl | H | mp. 93.4° C./(R*,R*) |
| 58 | 3 | $CH_3-CH_2$ | N | N | 4-F | H | mp. 185.4° C./(R*,R*) |
| 59 | 3 | $CH_3-CH_2$ | N | N | 3-Cl | H | mp. 160.0° C./(R*,R*) |
| 60 | 3 | $CH_3-CH_2$ | N | CH | 3-Cl | H | mp. 157.1° C./(R*,R*) |
| 61 | 3 | $CH_3-CH_2$ | N | CH | H | H | mp. 160.0° C./(R*,R*) |
| 62 | 3 | $CH_3-CH_2$ | N | CH | 3-Cl | 4-Cl | mp. 191.5° C./(R*,R*) |
| 63 | 3 | $CH_3-CH_2$ | N | CH | 4-F | H | mp. 180.0° C./(R*,R*) |
| 64 | 3 | $CH_3-CH_2$ | N | CH | 4-Br | H | mp. 202.0° C./(R*,R*) |
| 65 | 3 | $CH_3-CH_2$ | N | N | 3-Cl | 4-Cl | mp. 201.8° C./(R*,R*) |
| 66 | 3 | $CH_3-CH_2$ | N | N | 4-Br | H | mp. 213.3° C./(R*,R*) |
| 67 | 3 | $CH_3-CH_2$ | N | CH | 4-$CH_3$ | H | mp. 185.8° C./(R*,R*) |
| 68 | 3 | $CH_3-CH_2$ | N | N | 2-Cl | 4-Cl | mp. 184.5° C./(R*,R*) |
| 69 | 3 | $CH_3-CH_2$ | N | CH | 4-$OCH_3$ | H | mp. 174.9° C./(R*,R*) |
| 70 | 3 | $CH_3-CH_2$ | N | N | 4-$CH_3$ | H | mp. 162.2° C./(R*,R*) |
| 71 | 3 | $CH_3-CH_2$ | N | N | 4-$OCH_3$ | H | mp. 154.2° C./(R*,R*) |
| 5 | 5 | $CH_3-CH_2$ | N | CH | 4-F | H | mp. 161.2° C./[A-(R*,R*)] |
| 6 | 5 | $CH_3-CH_2$ | N | CH | 4-F | H | mp. 151.2° C./[B-(R*,R*)] |
| 72 | 3 | $CH_3-CH_2$ | N | CH | 3-Cl | 3-Cl | mp. 173.7° C./(R*,R*) |
| 73 | 3 | $C_6H_5-CH_2$ | N | N | 4-Cl | H | mp. 180.2° C./(R*,R*) |
| 86 | 3 | $(CH_3)_3C$ | N | N | 4-Cl | H | mp. 199.7° C./(R*,R*) |
| 87 | 3 | $(CH_3)_2CH$ | N | N | 4-Cl | H | mp. 197.4° C./(R*,R*) |
| 88 | 3 | $CH_3$ | N | N | 4-Cl | H | mp. 212.5° C./(R*,R*) |
| 89 | 3 | $CH_3$ | N | CH | 4-Cl | H | mp. 187.4° C./(R*,R*) |
| 90 | 3 | $CH_3-(CH_2)_2$ | N | CH | 4-Cl | H | mp. 175.9° C./(R*,R*) |
| 91 | 3 | $C_6H_5-CH_2$ | N | CH | 4-Cl | H | mp. 155.8° C./(R*,R*) |
| 92 | 3 | $CH_3-(CH_2)_3$ | N | CH | 4-Cl | H | mp. 150.3° C./(R*,R*) |
| 93 | 3 | $CH_3-CH_2$ | N | CH | 4-F | 2-F | mp. 154.4° C./(R*,R*) |

TABLE 3

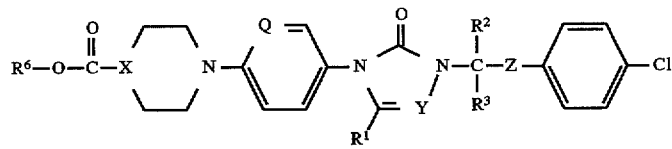

| Co No | Ex No | $R^6$ | X | Q | $R^1$ | Y | $R^2$ | $R^3$ | Z | Physical data |
|---|---|---|---|---|---|---|---|---|---|---|
| 94 | 3 | $CH_3CH_2$ | N | N | $CH_3$ | N | H | $CH_2CH_3$ | CHOH | mp. 174.6° C./(R*,R*) |
| 95 | 3 | $(CH_3)_2CH$ | N | N | $CH_3$ | N | H | $CH_2CH_3$ | CHOH | mp. 126.8° C./(R*,R*) |
| 96 | 3 | $CH_3CH_2$ | N | N | H | CH | H | $CH_2CH_3$ | CHOH | mp. 121.7° C./(R*,R*) |
| 97 | 3 | $CH_3CH_2$ | N | CH | H | CH | H | $CH_2CH_3$ | CHOH | mp. 136.2° C./(R*,R*) |
| 98 | 3 | $CH_3CH_2$ | N | CH | $CH_3$ | N | H | $CH_2CH_3$ | CHOH | mp. 131.8° C./(R*,R*) |
| 99 | 1 | $CH_3CH_2$ | N | CH | H | N | H | $(CH_2)_2CH_3$ | CO | mp. 148.9° C. |
| 100 | 1 | $CH_3CH_2$ | N | CH | H | N | H | H | CO | mp. 171.1° C. |
| 101 | 1 | $CH_3CH_2$ | N | N | $CH_3$ | N | H | H | CO | mp. 171.5° C. |
| 102 | 1 | $CH_3CH_2$ | N | N | H | N | H | $CH_3$ | CO | mp. 153.5° C. |
| 103 | 1 | $CH_3CH_2$ | N | CH | H | CH | H | $CH_2CH_3$ | CO | mp. 108.9° C. |
| 104 | 1 | $CH_3CH_2$ | N | CH | $CH_3$ | N | H | $CH_2CH_3$ | CO | mp. 150.6° C. |
| 105 | 1 | $CH_3CH_2$ | N | N | H | CH | H | $CH_2CH_3$ | CO | mp. 108.7° C. |
| 106 | 1 | $CH_3CH_2$ | N | N | $CH_3$ | N | H | $CH_2CH_3$ | CO | mp. 149.9° C. |
| 78 | 6 | $CH_3CH_2$ | N | CH | H | N | $CH_3$ | $CH_3$ | CO | mp. 137.0° C. |
| 79 | 7 | $CH_3CH_2$ | N | CH | H | N | $CH_3$ | $CH_3$ | CHOH | mp. 108.4° C. |
| 80 | 7 | $CH_3CH_2$ | N | CH | H | N | H | H | CHOH | mp. 208.5° C. |

TABLE 3-continued

| Co No | Ex No | R⁶ | X | Q | R¹ | Y | R² | R³ | Z | Physical data |
|---|---|---|---|---|---|---|---|---|---|---|
| 81 | 7 | $CH_3CH_2$ | CH | CH | H | N | H | $CH_2CH_3$ | CHOH | mp. 160.1° C. |
| 82 | 8 | $CH_3CH_2$ | N | N | H | N | H | $CH_2CH_3$ | CHOH | mp. 118.4° C. (R*,S*).½ $H_2O$ |
| 107 | 3 | $CH_3CH_2$ | N | N | H | N | H | $CH_3$ | CHOH | mp. 213.6° C. |
| 38 | 1 | $CH_3CH_2$ | N | CH | $CH_3$ | N | H | H | CO | mp. 192.0° C. |
| 108 | 3 | $CH_3CH_2$ | N | CH | H | N | H | $(CH_2)_2CH_3$ | CHOH | mp. 196.9° C. |

EXAMPLE 9

Pharmacological Example

The anti-Helicobacter activity of the subject compounds was assessed by the following in vitro test procedure.

Activity of Test Compounds Versus Helicobacter

The activity of test compounds against Helicobacter pylori was determined against a standard set of 5 H. pylori strains obtained from clinical material. Minimal inhibitory concentrations (MICs) were determined by measuring the activity of H. pylori urease after treatment of growing cultures of the bacteria with the antimicrobial agents.

The test compounds were dissolved in DMSO at a concentration of $10^{-3}$M. A dilution to $10^{-4}$M in DMSO was also prepared. 10 μl volumes of these solutions were pipetted in the wells of Repli-Dishes (®Sterilin). Wells containing DMSO alone were included as controls in each Repli-Dish. Ampicillin ((±)-6-[(2-amino-2-phenylacetyl)amino]-3,3-dimethyl-7-oxo-4-thia-1-azabicyclo[3.2.0]heptane-2-carboxylic acid.trihydrate) and metronidazole (2-methyl-5-nitro-1H-imidazol-1-ethanol) were included as reference compounds in each batch of tests (These compounds were tested at final concentrations of $10^{-5}$, $10^{-6}$, $10^{-7}$ and $10^{-8}$M). Test plates were stored at 4° C. until used.

The five isolates of H. pylori were maintained by subculture on 10% blood agar every 2 or 3 days. The bacteria were grown at 37° C. under an atmosphere containing 5% oxygen, 10% $CO_2$ and 85% nitrogen. Suspensions of Helicobacter pylori for inoculum were prepared in Brain-heart infusion broth and adjusted to an absorbance of 1.5±0.3 at 530 nM.

Freshly prepared 10% blood agar held at 45° C. was added in 1 ml volumes to the wells of the test plates, thus diluting the test compounds to $10^{-5}$ and $10^{-6}$M. The medium was allowed to cool, then 10 μl volumes of bacterial suspension were pipetted on the agar surface. The plates were incubated for 48 h at 37° C. under the microaerophilic atmosphere described above. To facilitate reading of the plates and to ensure that any growth on the media was truly H. pylori, advantage was taken of the highly potent urease activity unique to this species. After the 48 h of incubation, 1 ml volumes of urea broth were gently added to each Repli-Dish well and the plates were incubated at 37° C. for 2 h. 100 μl samples of fluid from each well were then pipetted into the wells of 96-place microdilution plates. A purple colour was interpreted as growth, yellow-orange as no growth of H. pylori. By this means a clear end-point was obtained, from which the inhibitory effects could be determined. All compounds that showed activity at either of the two concentrations tested were retested with further dilutions included to establish the MIC and with a broader spectrum of bacterial species as target organisms.

The MIC values for compound nos. 1–3, 5–6, 8–11, 13–28, 30–37, 39–43, 45–72, 74–77, 81–82, 88, 91–93, 96–98 and 102–107 were found to be equal or below 1 μM.

Composition Examples

"Active ingredient" (A.I.) as used throughout these examples relates to a compound of formula (I), a pharmaceutically acceptable acid addition salt or a stereochemically isomeric form thereof.

EXAMPLE 10

Oral Drops

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 11

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 12

Film-Coated Tablets

Preparation of tablet core

A mixture of 100 grams of the A.I., 570 grams lactose and 200 grams starch was mixed well and thereafter humidified with a solution of 5 grams sodium dedecyl sulfate and 10 grams polyvinylpyrrolidone in 200 ml of water. The wet powder mixture was sieved, dried and sieved again. 100 Grams microcrystalline cellulose and 15 grams hydrogenated vegetable oil were added. The whole was mixed well and compressed into tablets, giving 10.000 tablets, each containing 10 mg of the active ingredient.

Coating

To a solution of 10 grams methyl cellulose in 75 ml of denaturated ethanol was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 13

Suppositories

3 Grams A.I. was dissolved in a solution of 3 grams 2,3-dihydroxybutanedioic acid in 25 ml polyethylene glycol 400. 12 Grams surfactant and triglycerides q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

We claim:

1. A compound of the formula:

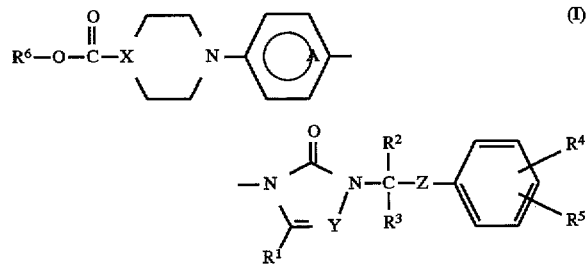
(I)

a pharmaceutically acceptable acid addition salt or a stereochemically isomeric form thereof, wherein:

Y is CH or N;

$R^1$, $R^2$ and $R^3$ each independently are hydrogen or $C_{1-4}$alkyl;

$R^4$ and $R^5$ each independently are hydrogen, halo, $C_{1-4}$alkyl, $C_{1-4}$alkyloxy, hydroxy, trifluoromethyl, trifluoromethyloxy or difluoromethyloxy;

$R^6$ is $C_{1-6}$alkyl, hydroxy$C_{1-6}$alkyl, $C_{1-4}$alkyloxy$C_{1-6}$alkyl, phenyl or phenyl $C_{1-4}$alkyl;

Z is CO or CHOH; and

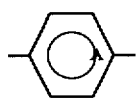

is a radical of the formula:

(a-1)

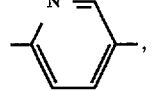
(a-2)

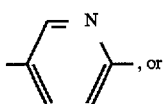
(a-3)

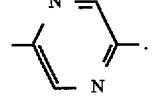
(a-7)

2. A compound according to claim 1 wherein $R^6$ is $C_{1-4}$alkyl.

3. A compound according to claim 2 wherein $R^2$ is $C_{1-4}$alkyl; $R^1$ and $R^3$ are hydrogen; $R^4$ is halo and $R^5$ is hydrogen or halo.

4. A compound according to claim 3 wherein said compound is ethyl 4-[5-[2-[1-[(4-chlorophenyl)hydroxymethyl]propyl]-2,3-dihydro-3-oxo-4H-1,2,4-triazol-4-yl]-2-pyridinyl]-1-piperazinecarboxylate;

ethyl 4-[4-[2-[1-[(4-chlorophenyl)hydroxymethyl]propyl]-2,3-dihydro-3-oxo-4H-1,2,4-triazol-4-yl]phenyl]-1-piperazinecarboxylate;

ethyl 4-[4-[2-[1-[(4-fluorophenyl)hydroxymethyl]propyl]-2,3-dihydro-3-oxo-4H-1,2,4-triazol-4-yl]phenyl]-1-piperazinecarboxylate;

a pharmaceutically acceptable addition salt or a stereochemically isomeric form thereof.

5. A pharmaceutical composition comprising a therapeutically effective amount of a compound as claimed in claim 1 and a pharmaceutically acceptable carrier.

6. A method for treating Helicobacter infection in patients in need of the same, which comprises administering to said patients an effective amount of a compound of claim 1.

7. A method for treating Helicobacter infection in patients in need of the same, which comprises administering to said patients an effective amount of a compound of claim 2.

8. A method for treating Helicobacter infection in patients in need of the same, which comprises administering to said patients an effective amount of a compound of claim 3.

9. A method for treating Helicobacter infection in patients in need of the same, which comprises administering to said patients an effective amount of a compound of claim 4.

10. A compound of the formula:

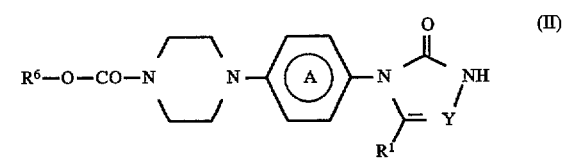
(II)

a pharmaceutically acceptable acid addition salt or a stereochemically isomeric form thereof, wherein $R^6$, $R^1$, and

are as defined in claim 1.

11. A method for treating Helicobacter infection in patients in need of the same, which comprises administering to said patients an effective amount of a compound of claim 1 and a proton pump inhibitor.

12. A method for treating Helicobacter infection in patients in need of the same, which comprises administering to said patients an effective amount of a compound of claim 2 and a proton pump inhibitor.

13. A method for treating Helicobacter infection in patients in need of the same, which comprises administering to said patients an effective amount of a compound of claim 3 and a proton pump inhibitor.

14. A method for treating Helicobacter infection in patients in need of the same, which comprises administering to said patients an effective amount of a compound of claim 4 and a proton pump inhibitor.

* * * * *

UNITED STATES PATENT AND TRADEMARK OFFICE
CERTIFICATE OF CORRECTION

PATENT NO.     : 5,710,156
DATED          : January 20, 1998
INVENTOR(S)    : Jan Heeres et al.

It is certified that error appears in the above-identified patent and that said Letters Patent is hereby corrected as shown below:

Column 21,
Lines 30-40, please delete the structure and insert therefore

-- 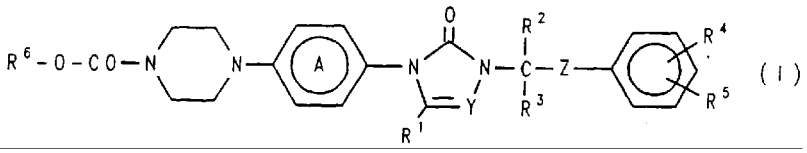 --

Signed and Sealed this

Seventh Day of September, 2004

JON W. DUDAS
*Director of the United States Patent and Trademark Office*